(12) United States Patent
Takeuchi et al.

(10) Patent No.: US 9,253,975 B2
(45) Date of Patent: Feb. 9, 2016

(54) TOOL FOR TRANSFERRING MEMBRANOUS TISSUE, KIT AND METHOD FOR TRANSFERRING MEMBRANOUS TISSUE

(75) Inventors: Ryohei Takeuchi, Kanagawa (JP); Tatsuya Shimizu, Tokyo (JP); Katsuhisa Sakaguchi, Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 839 days.

(21) Appl. No.: 13/470,271

(22) Filed: May 12, 2012

(65) Prior Publication Data
US 2013/0051969 A1    Feb. 28, 2013

(30) Foreign Application Priority Data
Aug. 26, 2011 (JP) ................. 2011-184760

(51) Int. Cl.
*A61B 18/18* (2006.01)
*A01N 1/02* (2006.01)
*A61B 17/00* (2006.01)

(52) U.S. Cl.
CPC ..... *A01N 1/0236* (2013.01); *A61B 2017/00747* (2013.01); *A61B 2017/00969* (2013.01)

(58) Field of Classification Search
CPC .................. A01N 1/0236; A61B 2017/00747; A61B 2017/00969
See application file for complete search history.

(56) References Cited

U.S. PATENT DOCUMENTS

| | | | |
|---|---|---|---|
| 5,653,713 A * | 8/1997 | Michelson | 606/83 |
| 6,514,238 B1 | 2/2003 | Hughes | |
| 2004/0206365 A1* | 10/2004 | Knowlton | 128/898 |
| 2004/0210214 A1* | 10/2004 | Knowlton | 606/41 |
| 2005/0197638 A1* | 9/2005 | Papendick et al. | 604/317 |
| 2009/0171159 A1* | 7/2009 | Jorgensen et al. | 600/139 |

FOREIGN PATENT DOCUMENTS

| | | |
|---|---|---|
| EP | 2 151 492 A1 | 2/2010 |
| GB | 1 584 392 A | 2/1981 |
| JP | 9-501065 A | 2/1997 |
| JP | 2001-507218 A | 6/2001 |
| JP | 2002-335950 A | 11/2002 |
| JP | 2008-43239 A | 2/2008 |
| JP | 2008-173333 A | 7/2008 |
| JP | 2010-75081 A | 4/2010 |
| WO | 94/21205 A1 | 9/1994 |
| WO | 98/24880 A1 | 6/1998 |
| WO | 2005/037986 A1 | 4/2005 |

OTHER PUBLICATIONS

The extended European Search Report for the related European Patent Application No. 12175916.1 dated Nov. 15, 2012.

* cited by examiner

*Primary Examiner* — Stephen Vu
(74) *Attorney, Agent, or Firm* — Kenealy Vaidya LLP (57) ABSTRACT

Disclosed herein is a tool, a kit, and associated method for transferring a membranous tissue composed of cells derived from a living body. The tool can include a first sheet-like supporting member disposed on one side of the membranous tissue in a wet state, and a second sheet-like supporting member disposed on the other side of the membranous tissue in a wet state. The first supporting member and the second supporting member can be configured to entirely hold the membranous tissue, such that a frictional force between the first supporting member and the membranous tissue is larger than a frictional force between the second supporting member and the membranous tissue.

19 Claims, 6 Drawing Sheets

FIG. 6C

TOOL FOR TRANSFERRING MEMBRANOUS TISSUE, KIT AND METHOD FOR TRANSFERRING MEMBRANOUS TISSUE This application claims the priority benefit under 35 U.S.C. §119 of Japanese Patent Application No. 2011-184760 filed on Aug. 26, 2011, which is hereby incorporated in its entirety by reference.

BACKGROUND

The presently disclosed subject matter relates to a tool for transferring a membranous tissue, which is capable of transferring a membranous tissue to a desired position for curing, a kit, and also to a method for transferring a membranous tissue through use of the tool.

Among recent common treatments for cardiac infarction and the like is transplantation of a cell sheet to the affected part. A "cell sheet" is a sheet-shaped cell culture which is obtained by culturing the cells of a patient until the patient's own cells form a tissue. The cell sheet is thin and fragile and highly self-adhesive due to its high water content; therefore, a sophisticated technique is usually used to accomplish transfer from the culture container to the affected part. In practice, this issue is addressed by using a special tool for transferring the sheet-shaped cell culture.

One conventional example of such transferring tools is disclosed in Japanese Patent Laid-open No. 2010-75081. The tool is composed of a cell sheet attracting section having a porous body and an evacuating section, so that the tool can transfer a cell sheet which has been picked up by the cell sheet attracting section by suction under reduced pressure.

Another example, as disclosed in Japanese Patent Laid-open No. 2008-173333, is a tool for transferring and applying a treating substance, which is composed of a sheet support to support a sheet-shaped treating substance (a cell sheet), means for deforming the sheet support, and sheet attaching-detaching means for selectively applying a negative pressure (which causes the cell sheet to be attracted to and held on the sheet support) and a positive pressure (which causes the cell sheet to be released).

SUMMARY

The presently disclosed subject matter was developed to address various characteristics, issues, and also various problems involved in transfer of a sheet-shaped cell culture. According to an aspect of the presently disclosed subject matter a tool can be provided for transferring a membranous tissue, which is designed such that it can hold a membranous tissue (such as a cell sheet) and transfer it to a desired position securely and easily despite having a simple structure, and also to provide a method for transferring a membranous tissue through use of the tool.

According to another aspect of the presently disclosed subject matter a tool for transferring a membranous tissue composed of cells, for example cells derived from a living body, can include a first sheet-like supporting member which is disposed on one side of a membranous tissue in a wet state and a second sheet-like supporting member which is disposed on the other side of a membranous tissue in a wet state such that the first supporting member and the second supporting member entirely hold the membranous tissue, with the first supporting member producing a larger frictional force than the second supporting member during their contact with the membranous tissue.

The tool for transferring a membranous tissue, which is constructed as mentioned above, is used as follows. First, it is placed on the position (or organ) to which the membranous tissue is to be transferred. Then, the second supporting member between the membranous tissue and the position for transfer is removed. Finally, the first supporting member on the membranous tissue is removed, with the membranous tissue remaining on the position for transfer. Thus, the membranous tissue can be transferred to the desired position in a secure and simple way without damage to it.

The above-mentioned tool for transferring a membranous tissue includes a first supporting member that is thinner than the second supporting member so that the former has a stronger tendency toward cohesion to the membranous tissue than the latter. The greater the cohesion force between the two elements, the larger the frictional force between the two elements. The consequence of the fact that the first supporting member is thinner than the second supporting member is that the frictional force between the first supporting member and the membranous tissue is larger than that between the second supporting member and the membranous tissue.

Moreover, the above-mentioned tool for transferring a membranous tissue includes a first supporting member that is more flexible than the second supporting member so that the first supporting member easily follows the pulsation of the organ to which the membranous tissue is transferred. This helps prevent damage to the membranous tissue. Also, the flexible first supporting member can be easily peeled off because it is folded back with a small radius of curvature at the time of peeling from the membranous tissue.

The above-mentioned tool for transferring a membranous tissue also includes a first supporting member and a second supporting member that hold between them a holding unit that holds the membranous tissue thereon. The tool for transferring a membranous tissue may also have a third supporting member which is stiffer than the second supporting member, and the holding unit is placed on the third supporting member so that the holding unit is moved easily and securely to the position for transfer.

The above-mentioned tool for transferring a membranous tissue is also configured so that at least either of the first and second supporting members has a grip (which is stiffer than other parts) on at least one portion of one edge thereof. This grip helps to easily remove either or both of the first and second supporting members.

In addition, the presently disclosed subject matter provides a method for transferring a membranous tissue composed of cells derived from a living body. The method includes a first process of preparing a tool for transferring a membranous tissue, the tool having a first sheet-like supporting member which is disposed on one side of the membranous tissue in a wet state and a second sheet-like supporting member which is disposed on the other side of the membranous tissue in a wet state such that the first supporting member and the second supporting member entirely hold the membranous tissue, with the first supporting member producing a larger frictional force than the second supporting member during their contact with the membranous tissue, a second process of arranging the tool for transferring a membranous tissue on the position to which the membranous tissue is transferred, a third process of sliding the second supporting member relative to the membranous tissue, thereby removing the second supporting member from the gap between the membranous tissue and the position to which the membranous tissue is transferred, and a fourth process of removing the first supporting member from the top of the membranous tissue while leaving the membranous tissue on the position to which the membranous tissue is transferred.

The foregoing method permits the membranous tissue to be transferred to a desired position simply and securely without damage thereto.

The presently disclosed subject matter also provides a method for transferring a membranous tissue composed of cells derived from a living body. The method includes a first process of preparing a tool for transferring a membranous tissue, the tool having a first sheet-like supporting member which is disposed on one side of the membranous tissue in a wet state and a second sheet-like supporting member which is disposed on the other side of the membranous tissue in a wet state such that the first supporting member and the second supporting member entirely hold the membranous tissue, with the first supporting member producing a larger frictional force than the second supporting member during their contact with the membranous tissue, a second process of arranging the tool for transferring a membranous tissue in the neighborhood of the position to which the membranous tissue is transferred, a third process of sliding the first supporting member and membranous tissue relative to the second supporting member, thereby placing the first supporting member and membranous tissue on the position for transfer, and a fourth process of removing the first supporting member from the membranous tissue while leaving the membranous tissue on the position for transfer.

The foregoing method permits the membranous tissue to be transferred to a desired position simply and securely without damage thereto.

According to another aspect of the disclosed subject matter a kit for transferring a membranous tissue composed of cells can include the membranous tissue, a preserving liquid, and first and second sheet-like supporting members. The first sheet-like supporting member can be disposed on one side of the membranous tissue in a wet state, and the second sheet-like supporting member can be disposed on the other side of the membranous tissue in a wet state. The first supporting member and the second supporting member can be configured to entirely hold the membranous tissue, and the first supporting member and the second supporting member can also be configured such that a frictional force between the first supporting member and the membranous tissue is larger than a frictional force between the second supporting member and the membranous tissue. The kit can consist of only the first sheet-like supporting member, the second sheet-like supporting member, the membranous tissue, and the preserving liquid located between the first and second sheet-like supporting members with the membranous tissue located in the preserving liquid. Alternatively, the kit can include one or more of a separate container for the preserving liquid, a separate container for the membranous tissue, and a separate container for the first and second sheet-like supporting members. In addition, the kit could include multiple of the same elements. For example, the kit could include a matrix of first and second sheet-like supporting members that can be separately obtained from the kit for use with a particular membranous tissue. Further, the kit could include multiple first and second sheet-like supporting members that already include the preserving liquid and membranous tissue located therebetween.

The presently disclosed subject matter provides a tool for transferring a membranous tissue, a kit, and a method for transferring a membranous tissue through use of the tool. Despite its simple structure, the tool easily and securely holds and transfers a membranous tissue (which is a cell culture in sheet form) to a desired position.

DETAILED DESCRIPTION OF EXEMPLARY EMBODIMENTS

The following is a detailed description of exemplary embodiments of a tool for transferring a membranous tissue made in accordance with principles of the presently disclosed subject matter, which refers to the accompanying drawings.

Figure 1A:
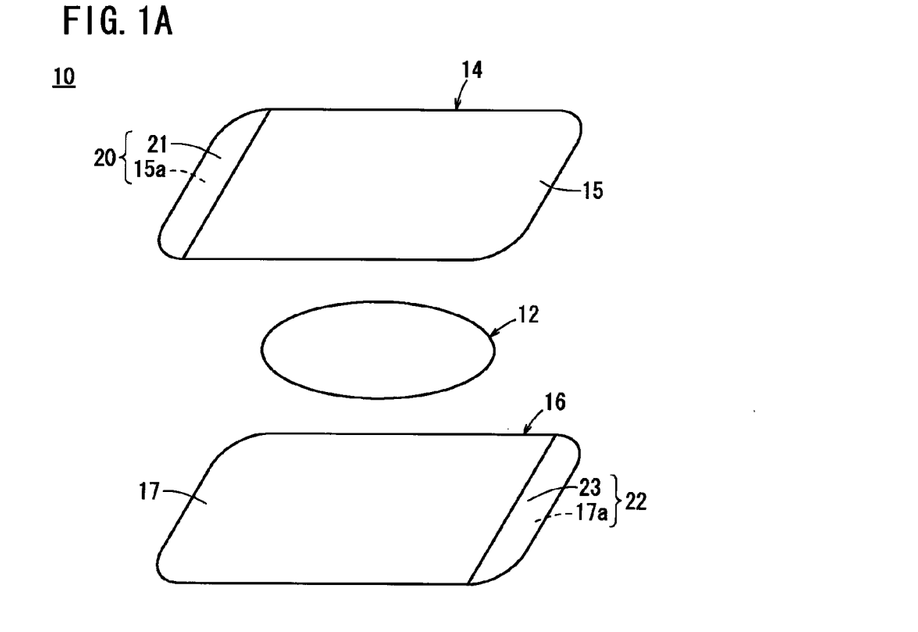
FIG. 1A is an exploded perspective view showing an example of a tool for transferring a membranous tissue according to a first embodiment of the presently disclosed subject matter.
Figure 1B:
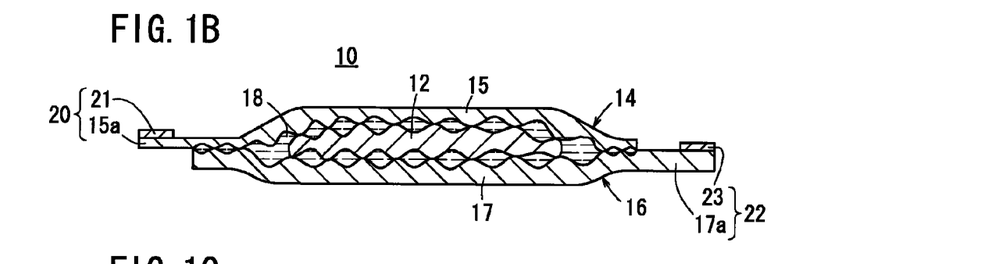
FIG. 1B is a sectional view of the tool for transferring a membranous tissue shown in FIG. 1A.
Figure 1C:
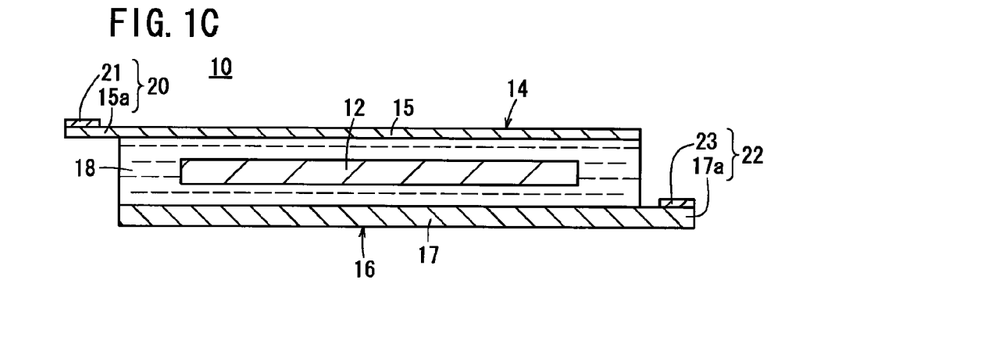
FIG. 1C is a simplified schematic sectional view of FIG. 1B.

FIG. 1A is an exploded perspective view showing a tool 10 for transferring a membranous tissue according to the first embodiment of the presently disclosed subject matter. (This tool will be simply referred to as the transferring tool 10 hereinafter.) FIG. 1B is a sectional view of the transferring tool 10. FIG. 1C is a schematic sectional view of the transferring tool 10. Incidentally, FIG. 1B is an exaggerated diagram, with each constituent appearing larger in thickness, space, and irregularity than the actual device. In addition, FIG. 1C schematically shows the transferring tool 10 shown in FIG. 1B in a further simplified manner for easy understanding.

As shown in FIGS. 1A to 1C, the transferring tool 10 can be composed of a membranous tissue 12 to be transferred, a first supporting member 14 arranged on one side of the membranous tissue 12 (or at the upper side in FIG. 1A), and a second supporting member 16 arranged on the other side of the membranous tissue 12 (or at the lower side in FIG. 1A). The transferring tool 10 can be used to transfer (graft) the membranous tissue 12 to that part of the living body which needs treatment (or to the position for transfer). The position for transfer to which the membranous tissue 12 is applied includes culture containers, organs (such as heart, esophagus, lung, and cornea), skin, and other locations depending on the particular surgical or laboratory application.

The membranous tissue 12 is an object having a certain thickness which may be derived from a living body. The membranous tissue 12 can be used for regeneration, curing, and to cure or prevent acceleration of disorders, cure diseases and remedy defective features, injuries, and/or malformations in part or all of tissue or in one or more of organs such as heart, cornea, retina, blood vessel, nerve, epidermis, dermis, cartilage, tooth, and other depending on application. It can also be used to test drugs for irritation, sensitivity, toxicity, effect, and reaction on organs and tissues. The membranous tissue 12 can be a sheet-shaped cell culture prepared from skin tissue, mucous epithelium tissue, cornea epithelium tissue, cultured skin, cultured dermis, cultured epidermis, cultured epidermis tissue, cultured cornea tissue, cartilage tissue, retina tissue, nerve filament, artificial blood vessel, myoblast tissue, and the above-mentioned cells derived from a living body, or other cell culture depending on particular application. In one example, a sheet-shaped cell culture can be prepared from myoblasts. The membranous tissue 12 may be composed only of cells or cell secreta, but it may also contain substance(s) which is/are not derived from a living body. The membranous tissue 12 is, in many cases, thin and fragile.

The membranous tissue 12 can be arranged (in a wet state) between the first supporting member 14 and the second supporting member 16. Furthermore, the membranous tissue 12 can be kept wet by a preserving liquid 18, so that it retains its biological characteristic properties. Examples of the preserving liquid 18 include liquid culture media, physiological saline, isotonic solution, buffer solution, and Hank's balanced salt solution.

Incidentally, FIG. 1C is schematic in nature because it depicts the membranous tissue 12 as if it were floating in the preserving liquid 18 between the first supporting member 14 and the second supporting member 16. In actual fact, however, each of the membranous tissue 12, the first supporting member 14, and the second supporting member 16 has minute surface irregularities through which they are in contact with one another. The first supporting member 14 and the membranous tissue 12 are in contact at least partly with each other, with other parts slightly separated from each other by the preserving liquid 18 present between them. This also holds true for the relation between the second supporting member 16 and the membranous tissue 12. In addition, as shown in FIG. 1B, one end of the first supporting member 14 is sealed against the second supporting member 16 and one end of the second supporting member 16 is sealed against the first supporting member 14, so that the gap between the two supporting members is closed. FIGS. 2A to 2D, 3A to 3C, and 5A to 5C are diagrams schematized in the same way as FIG. 1C.

The first supporting member 14 can be configured as a sheet-like member which is arranged on one side (top) of the membranous tissue 12 so that it entirely covers one side of the membranous tissue 12. It is larger in size than the membranous tissue 12.

The second supporting member 16 can be configured as a sheet-like member which is arranged on the other side (bottom) of the membranous tissue 12 so that it entirely covers the other side of the membranous tissue 12. It is larger in size than the membranous tissue 12. The first and second supporting members 14 and 16 can take on an approximately thin sheet-like shape, and can be formed from a flexible material.

The transferring tool 10 pertaining to this embodiment is characterized in that the first supporting member 14 is composed of a first sheet-like body 15 (as the major constituent) and a grip 20 attached to one end of the first sheet-like body 15. The grip 20 is stiffer than the first sheet-like body 15. In the illustrated example, it is a straight slip including a reinforcing sheet 21 bonded to an edge 15a of one end of the first sheet-like body 15. In other words, the grip 20 is composed of the edge 15a of the first sheet-like body 15 and the slip of the reinforcing sheet 21. The reinforcing sheet 21 is formed from a film (with a prescribed thickness) of any material similar or dissimilar to the material for the first sheet-like body 15.

In the transferring tool 10, the second supporting member 16 is composed of a second sheet-like body 17 (as the major constituent) and a grip 22 attached to one end of the second sheet-like body 17. The grip 22 is stiffer than the second sheet-like body 17. In the illustrated example, it is a straight slip including a reinforcing sheet 23 bonded to an edge 17a of one end of the second sheet-like body 17. In other words, the grip 22 is composed of the edge 17a of the second sheet-like body 17 and the slip of the reinforcing sheet 23. The reinforcing sheet 23 is formed from a film (with a prescribed thickness) of any material similar or dissimilar to the material for the second sheet-like body 17.

The first supporting member 14 and the second supporting member 16 face each other, with the former's ends shifted from the latter's ends. In other words, one end of the first supporting member 14 (or the end to which the grip 20 is attached in FIG. 1B) projects from the end of the second supporting member 16, and an other end of the second supporting member 16 (or the end to which the grip 22 is attached in FIG. 1B) projects from the end of the first supporting member 14.

In the illustrated example, the grips 20 and 22 are attached respectively to respective ends of the first and second supporting members 14 and 16 which are opposite to each other. However, they may be attached to ends located at the same sides.

In the illustrated example, the first and second supporting members 14 and 16 are similar to each other in size and shape or they are rectangular, with rounded corners, in plan view. Incidentally, the first and second supporting members 14 and 16 are not restricted in their shape; they may take on shapes other than a rectangle (shown in FIG. 1), such as circular, elliptical, square or even non-symmetrical.

As mentioned above, the membranous tissue 12 is kept wet by the preserving liquid 18, and this wet state is maintained while it is held between the first and second supporting members 14 and 16. The membranous tissue 12 is thin and the gap between the first and second supporting members 14 and 16 is narrow, so that the preserving liquid 18 is held between them by its surface tension. The first and second supporting members 14 and 16 can be sufficiently transparent so that the membranous tissue 12 held between them is visible through them.

The first and second sheet bodies 15 and 17 can be formed from a material which is flexible (as mentioned above) and can be strong enough to securely support the membranous tissue 12 without causing damage to it while being compatible with the living body. The foregoing material may be selected from such polymeric materials as polyolefins (including polyethylene, polypropylene, polybutene, ethylenepropylene copolymer, ethylene-vinyl acetate copolymer, ionomer, and mixtures of two or more of them), polyvinyl chloride, polyamide, polyamide elastomer, polyurethane, polyurethane elastomer, polyimide, and fluoroplastics, mixtures thereof, and other similar materials.

The exemplary transferring tool 10 is characterized in that the frictional force P1 between the first supporting member 14 (or the first sheet body 15) and the membranous tissue 12 is greater than the frictional force P2 between the second supporting member 16 (or the second sheet body 17) and the membranous tissue 12. According to this embodiment, the frictional force between the first supporting member 14 and the membranous tissue 12 is made larger than that between the second supporting member 16 and the membranous tissue 12 by employing the first supporting member 14 (or the first sheet body 15) and the second supporting member 16 (or the second sheet body 17) which differ in thickness, with the former being thinner than the latter. The following is a description of the reason why the frictional forces P1 and P2 vary accordingly as the first and second supporting members 14 and 16 vary in thickness.

If there exists water between two objects in contact with each other, a frictional force occurs between them due to cohesive force resulting from "pressure decrease by surface tension (or Laplace pressure)" and "direct action by surface tension." "Laplace pressure" represents the pressure (negative pressure) induced by water droplets (liquid crosslinking) on the two surfaces, and it is denoted by the formula (1) below. "Direct action by surface tension" is denoted by the formula (2) below.

$$F_1 = \pi r^2 s/(h/2) \qquad (1)$$

$$F_2 = \pi ds \qquad (2)$$

In the formulas (1) and (2) above, r denotes the radius of the water droplet, d denotes the diameter of the water droplet, s denotes the surface tension, and h denotes the distance between the two surfaces. It is to be noted from the formulas (1) and (2) that the smaller the distance between the two surfaces, the greater the Laplace pressure, and the larger the diameter of the water droplet, the greater the direct action of surface tension and the Laplace pressure. The frictional force is represented by the frictional coefficient multiplied by the vertical drag. However, under special conditions of very small weight, the frictional force is an action of the cohesive force as a vertical drag. Therefore, the frictional force is represented by the frictional coefficient multiplied by the sum of the cohesive force and the vertical drag. This means that the frictional force can be controlled if the cohesive force is controlled.

K. Kendall, "The adhesion and surface energy of elastic solids," J. Phys. D: Appl. Phys., 1971, vol. 4. reports that the relation between the film thickness and the cohesive force is represented by the formula (3) below.

$$P^2 = 2\pi^2 K \gamma a^4/t \qquad (3)$$

In the formula (3), P denotes cohesive force, K denotes bulk modulus, γ denotes surface free energy, a denotes radius of contact area, and t denotes film thickness. This formula suggests that the smaller the film thickness, the greater the cohesive force. Since the frictional force equals the frictional coefficient multiplied by the sum of the cohesive force and the vertical drag as mentioned above, the film thickness affects the magnitude of the frictional force.

Based on the foregoing theory, this embodiment is characterized in that the first sheet body 15 is thinner than the second sheet body 17 so that the frictional force P1 between the first sheet body 15 and the membranous tissue 12 is greater than the frictional force P2 between the second sheet body 17 and the membranous tissue 12. In addition, the first sheet body 15 is thinner than the second sheet body 17, so that the former is more flexible than the latter.

According to this embodiment, in which the frictional force P1 is greater than the frictional force P2, the transferring tool 10 is constructed such that the second supporting member 16 can be removed from between the membranous tissue 12 and the position for transfer while the membranous tissue 12 remains immobile relative to the first supporting member 14. (This will be described in more detail later.) Consequently, the ratio of the frictional force P1 to the frictional force P2 is 125% or higher, and possibly 200% or higher. And, the ratio of the thickness of the first sheet body 15 to the thickness of the second sheet body 17 is 80% or smaller, and possibly 50% or smaller.

The first sheet body 15 and the second sheet body 17 can be configured to have adequate flexibility so that the transferring tool 10 placed on the position for transfer (such as culture container and/or organs) readily deforms along the shape of the surface of the position for transfer. For this reason, the first sheet body 15 can have a thickness of 0.01 to 200 μm, and possibly 1 to 100 μm, for example. The second sheet body 17 can have a thickness of 10 to 500 μm, and possibly 50 to 200 μm, for example. With an excessively small thickness, the first and second sheet bodies 15 and 17 may not have sufficient strength to securely hold the membranous tissue 12. Conversely, with an excessively large thickness, the first and second sheet bodies 15 and 17 may not have sufficient flexibility to allow the transferring tool 10 placed on the position for transfer (such as culture container and organs) to readily deform along the shape of the surface of the position for transfer.

The transferring tool 10 according to this embodiment is basically constructed as mentioned above. Exemplary function and effect are described below.

Figure 2A:
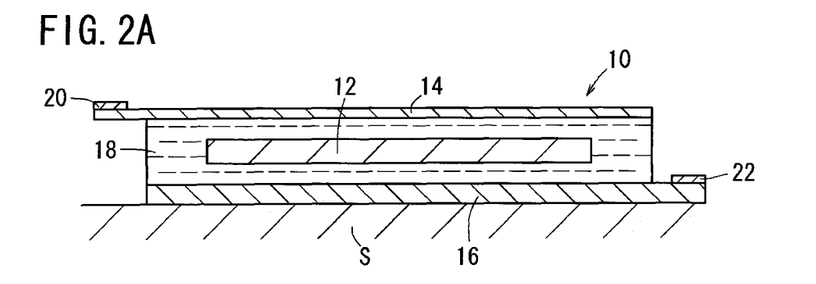
FIG. 2A is a diagram illustrating an example of a first process in the procedure for transferring a membranous tissue to a desired position for transfer by using the exemplary tool for transferring a membranous tissue as shown in FIG. 1.

An exemplary process for transferring (grafting) the membranous tissue 12 to the desired position for transfer by using the transferring tool 10 starts with arranging the transferring tool 10 on the position for transfer S, as shown in FIG. 2A. The position for transfer S may be a culture container or an organ or skin of a living body (human and other mammals), or other.

Figure 2B:
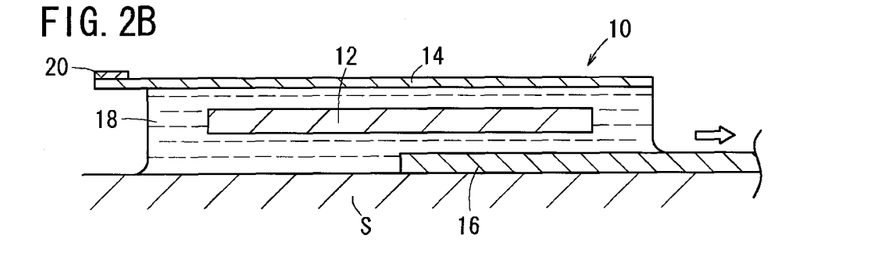
FIG. 2B is a diagram illustrating an example of a second process in the procedure.

Then, the second supporting member 16 is slid relative to the membranous tissue 12, so that the second supporting member 16 is removed from between the membranous tissue 12 and the position for transfer S as shown in FIG. 2B. The procedure for sliding the second supporting member 16 can be accomplished easily by pulling the stiff grip 22, which is attached to one end of the second supporting member 16, possibly with the help of a grip holder or the like. Incidentally, the grip 22 may be attached to both ends of the second supporting member 16. This structure permits one to work freely by holding either of the two grips.

Since the frictional force P1 between the first supporting member 14 and the membranous tissue 12 is greater than the frictional force P2 between the second supporting member 16 and the membranous tissue 12, as mentioned above, the membranous tissue 12 remains unremoved owing to the frictional forces P1 between the first supporting member 14 and the membranous tissue 12 when the second supporting member 16 is slid, with the first supporting member 14 remaining stationary. In this way, the second supporting member 16 alone is removed while the membranous tissue 12 remains at its original place.

Figure 2C:
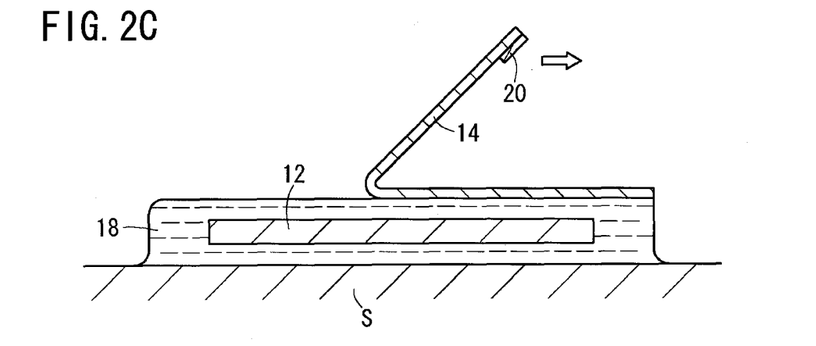
FIG. 2C is a diagram illustrating an example of a third process in the procedure.

Subsequently, the first supporting member 14 is removed from the top of the membranous tissue 12, with the membranous tissue 12 remaining on the position for transfer S, as shown in FIG. 2C. To be more specific, the first supporting member 14 can be removed by holding one edge of the first supporting member 14 in such a way that the first supporting member 14 is folded back and peeled off. This procedure can be accomplished easily by holding the stiff grip 20, which is attached to one end of the first supporting member 14, possibly with the help of a grip holder or the like. As the first supporting member 14 is removed as mentioned above, the membranous tissue 12 is transferred to the position for transfer S. Incidentally, the grip 20 may be attached to both ends of the first supporting member 14. This structure permits one to work freely by holding either of the two grips.

The procedure shown in FIG. 2C is carried out in such a way that the first supporting member 14 is peeled off from that side thereof which is opposite (the left side in FIG. 2C) to the direction in which the second supporting member 16 is slid. However, it is also possible to peel off the first supporting member 14 from that side thereof which is coincident (the right side in FIG. 2C) with the direction in which the second supporting member 16 is slid. In this case, the grip 20 may be attached to that end extending in the direction in which the second supporting member 16 is slid.

Figure 2D:
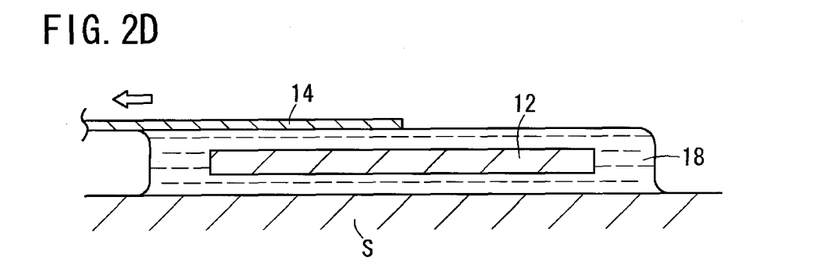
FIG. 2D is a diagram illustrating a modified example of the third process in the procedure.

The procedure shown in FIG. 2C may be replaced by the one shown in FIG. 2D, which permits the first supporting member 14 to be removed by sliding the first supporting member 14 from the top of the membranous tissue 12, with the membranous tissue 12 being left on the position for transfer S. The procedure shown in FIG. 2D is carried out in such a way that the first supporting member 14 is slid in the direction (to the left in FIG. 2D) opposite to the direction in which the second supporting member 16 is slid. However, it is also possible to slide the first supporting member 14 in the same direction as the direction in which the second supporting member 16 is slid.

The transferring tool 10 according to the embodiment mentioned above is designed such that it is placed on the position for transfer S (which is an organ or the like), and then only the second supporting member 16 is removed from between the membranous tissue 12 and the position for transfer S, and finally the first supporting member 14 is removed from the top of the membranous tissue 12, with the membranous tissue 12 remaining on the position for transfer S. In this way the membranous tissue 12 can be simply and securely transferred to the position for transfer S without damage to the membranous tissue 12.

According to this embodiment, the first supporting member 14 (or the first sheet body 15) is thinner than the second supporting member 16 (or the second sheet body 17), so that the cohesive force between the first supporting member 14 and the membranous tissue 12 is greater than that between the second supporting member 16 and the membranous tissue 12. The result is that the frictional force P1 between the first supporting member 14 and the membranous tissue 12 is greater than the frictional force P2 between the second supporting member 16 and the membranous tissue 12.

In addition, according to this embodiment, the first supporting member 14 is more flexible than the second supporting member 16. Therefore, the first supporting member 14 easily follows the pulsation of the organ (such as heart) at the position for transfer S. This helps prevent damage to the membranous tissue 12.

Moreover, the fact that the first supporting member 14 is flexible permits it to be folded back sharply as shown in FIG. 2C when it is peeled off from the membranous tissue 12. The sharp folding reduces the surface tension at the folded part, and this facilitates the peeling of the first supporting member 14. As a result, the first supporting member 14 can be easily peeled off from the membranous tissue 12, while the membranous tissue 12 is left with some degree of certainty on the position for transfer S.

Figure 3A:
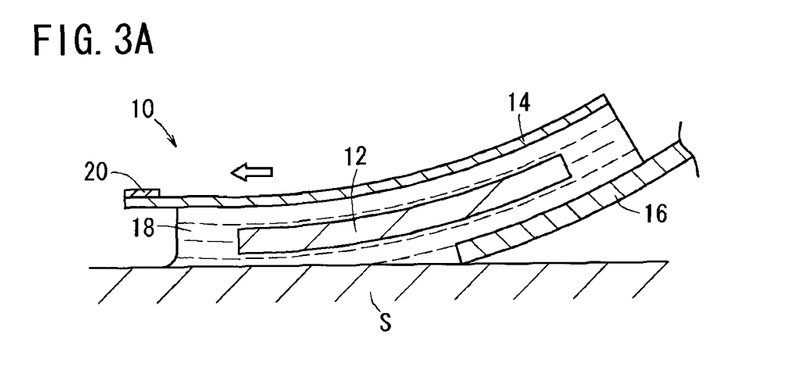
FIG. 3A is a diagram illustrating an example of a first process in a second exemplary procedure for transferring a membranous tissue to a desired position for transfer by using the tool for transferring a membranous tissue as shown in FIG. 1.
Figure 3B:
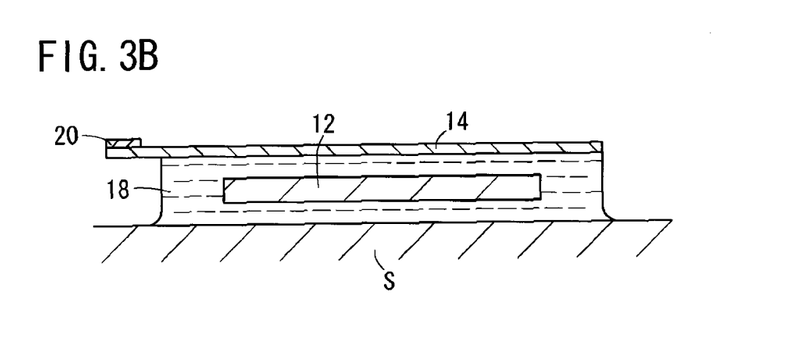
FIG. 3B is a diagram illustrating an example of a second process in the second exemplary procedure.
Figure 3C:
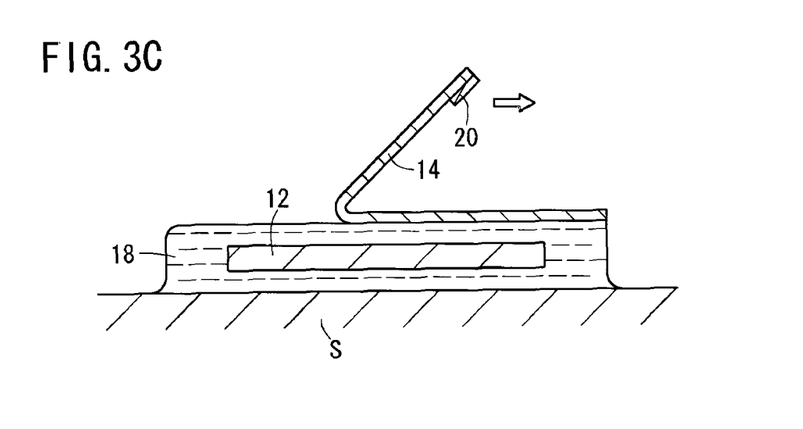
FIG. 3C is a diagram illustrating an example of a third process in the second exemplary procedure.

The procedure for transferring the membranous tissue 12 to the position for transfer S through use of the transfer tool 10 can be accomplished as illustrated in FIGS. 2A to 2D. This procedure (designated as the first procedure) may be replaced with another one (for example, the second procedure) which is illustrated in FIGS. 3A to 3C. The second procedure starts with placing the transferring tool 10 in the neighborhood of the position for transfer S. In the next step, the first supporting member 14 and the membranous tissue 12 are slid relative to the second supporting member 16, as shown in FIG. 3A. During this step, the first supporting member 14 and the membranous tissue 12 slide together as the first supporting member 14 is slid (by holding the grip) because the frictional force P1 between the first supporting member 14 and the membranous tissue 12 is greater than the frictional force P2 between the second supporting member 16 and the membranous tissue 12.

The first supporting member 14 and the membranous tissue 12 are arranged on the position for transfer S by sliding the first supporting member 14 and the membranous tissue 12 all together, as shown in FIG. 3B. Then, the first supporting member 14 is removed from the top of the membranous tissue 12 while the membranous tissue 12 is left on the position for transfer S, as shown in FIG. 3C. The procedure shown in FIG. 3C is identical with that shown in FIG. 2C. Incidentally, the procedure shown in FIG. 3C may be replaced by the one shown in FIG. 2D.

The second procedure for transfer also permits one to transfer the membranous tissue 12 to the desired position for transfer S easily and securely without damage to the membranous tissue 12.

The examples of experiments and some working examples of the disclosed subject matter will be described below.

EXPERIMENT EXAMPLES

Preparation of Membranous Tissue

Experiment Example 1

Preparation of a Sheet-Shaped Cell Culture from Human Myoblasts

Human skeletal myoblasts (produced by Lonza) were inoculated on DMEM/F12 culture medium containing 20% human serum (produced by Invitrogen) which is held in a temperature-responsive cell culture dish (UpCell®, 3.5 cm or 10.0 cm in diameter, made by Cellseed), at a density of $10^6$ cells per $cm^2$. Cultivation at 37° C. for 24 hours in 5% $CO_2$ yielded a single layer sheet. With the culture dish cooled to 20° C., the sheet-shaped cell culture was removed from the culture dish. The resulting sheet-shaped cell culture measured approximately 15 mm or 45 mm in diameter and approximately 30 µm to 60 µm in thickness.

Experiment Example 2

Preparation of a Sheet-Shaped Cell Culture from Pig Myoblasts

Pig skeletal myoblasts were isolated as follows by the method disclosed in Japanese Patent Laid-open No. 2007-

89442. First, skeletal muscle was taken from the lower extremity of a miniature pig (purchased from Nisseiken Co., Ltd.). Then, the muscle was washed by immersion in a tissue transfer solution (HBSS, made by GIBCO), containing 1.45 mg/mL of glucose (made by Otsuka Pharmaceutical Co., Ltd.), 0.1 mg/mL of gentamicin (made by Fuji Seiyaku), and 2.5 μg/mL of fungizone (made by GIBCO).

The skeletal muscle was cut into small pieces (each measuring 2 mm square or less) in an enzyme solution (TrypLE Select, made by Invitrogen) containing 0.5 mg/mL of collagenase A (made by Nippon Roche), 50 μg/mL of gentamicin (made by Fuji Seiyaku), and 0.25 μg/mL of fungizone (made by GIBCO). The resulting pieces were freed of white tissues (connective tissues). The thus obtained tissues were cut into small pieces and stirred in the enzyme solution mentioned above kept at 37° C. in a thermostat for 60 minutes. After enzyme treatment, the resulting liquid containing cells floating therein were collected by suction and centrifuged. The supernatant fluid was discarded to recover the cells. The step for enzyme treatment was repeated several times so as to collect pig skeletal myoblasts.

The thus obtained pig skeletal myoblasts were inoculated on MCDB 131 culture medium (made by Invitrogen) containing 20% of fetal bovine serum (made by Invitrogen), 4% of L-glutamine (made by Invitrogen), 0.01 μg/mL of epidermal growth factor (made by Invitrogen), and 4 μg/mL of dexamethazone sodium phosphate (made by Schering-Plough), and were held in a temperature-responsive cell culture dish (UpCell®, 6 cm or 10.0 cm in diameter, made by Cellseed) at a density of $10^6$ cells per $cm^2$. Cultivation at 37° C. for 24 hours in 5% $CO_2$ yielded a sheet. With the culture dish cooled to 20° C., the sheet-shaped cell culture was removed from the culture dish. The resulting sheet-shaped cell culture measured approximately 25 mm or 45 mm in diameter and approximately 30 μm to 60 μm in thickness.

Experiment Example 3

Preparation of a Sheet-Shaped Cell Culture from Mouse Fibroblasts (NIH3T3)

Mouse fibroblasts (NIH3T3 cells) were inoculated on DMEM culture medium (made by Invitrogen) containing 20% of fetal bovine serum (made by Invitrogen), and were held in a temperature-responsive cell culture dish (UpCell®, 10.0 cm in diameter, made by Cellseed), at a density of $10^6$ cells per $cm^2$. Cultivation at 37° C. for 24 hours in 5% $CO_2$ yielded a single layer sheet. With the culture dish cooled to 20° C., the sheet-shaped cell culture was removed from the culture dish. The resulting sheet-shaped cell culture measured approximately 45 mm in diameter and approximately 30 μm to 60 μm in thickness.

EXAMPLES

The following examples show the results of the tests which were performed to confirm the effect of the presently disclosed subject matter.

Example 1

Experiment with Films of the Same Material

Example 1-1

The first supporting member: 68-μm thick film of polyethylene

The second supporting member: 168-μm thick film of polyethylene

Membranous tissue: sheet-shaped cell culture prepared from human myoblasts

Position for transfer: culture container

Method: A transferring tool was prepared and composed of the first supporting member and the second supporting member, with the membranous tissue (kept wet with water) held between them. The second supporting member was slid, with the first supporting member kept stationary, in the same way as shown in FIG. 2B.

Result: The sliding of the second supporting member did not move the membranous tissue, with the first supporting member remaining stationary. This result suggests that the frictional force between the first supporting member and the membranous tissue is greater than that between the second supporting member and the membranous tissue.

Example 1-2

The first supporting member: 10-μm thick film of polyurethane

The second supporting member: 110-μm thick film of polyurethane

Membranous tissue: sheet-shaped cell culture prepared from human myoblasts

Position for transfer: culture container

Method: same as in Example 1-1

Result: The sliding of the second supporting member did not move the membranous tissue, with the first supporting member remaining stationary. This result suggests that the frictional force between the first supporting member and the membranous tissue is greater than that between the second supporting member and the membranous tissue.

Example 2

Experiment with Films of Dissimilar Materials, in which the Position for Transfer is a Curved Surface Example 2-1

The first supporting member: 25-μm thick film of polyurethane

The second supporting member: 68-μm thick film of polyethylene

Membranous tissue: sheet-shaped cell culture prepared from human myoblasts

Position for transfer: artificial organ (clay wrapped in food-wrapping film), having a curved surface.

Method: A transferring tool was prepared and composed of the first supporting member and the second supporting member, with the membranous tissue (kept wet with water) held between them. Transfer was accomplished by the method shown in FIGS. 2A to 2C.

Result: In the step shown in FIG. 2B, it was possible to remove the second supporting member alone while keeping the membranous tissue stationary. Thus, it was possible to transfer the membranous tissue without damage to it. The transferring tool easily deformed to closely adhere to the surface of the artificial organ even though the surface was sharply bent. Since polyurethane and polyethylene are similar to each other in terms of bulk modulus and surface free energy, the difference between the frictional force between the first supporting member and the membranous tissue and the frictional force between the second supporting member and the membranous tissue results from the difference in thickness between the first supporting member and the second supporting member.

Example 2-2

The first supporting member: 25-μm thick film of polyurethane

The second supporting member: 195-μm thick film of polypropylene

Membranous tissue: sheet-shaped cell culture prepared from human myoblasts

Position for transfer: artificial organ (clay wrapped in food-wrapping film), having a curved surface.

Method: A transferring tool was prepared and composed of the first supporting member and the second supporting member, with the membranous tissue (kept wet with water) held between them. Transfer was accomplished by the method shown in FIGS. 3A to 3C.

Result: In the step shown in FIG. 3A, the first supporting member was slid relative to the second supporting member by grasping the first supporting member. This action caused the membranous tissue to slide, together with the first supporting member, relative to the second supporting member. Thus it was possible to arrange the membranous tissue, together with the first supporting member, on the position for transfer. Since polyurethane and polypropylene are similar to each other in terms of bulk modulus and surface free energy, the difference between the frictional force between the first supporting member and the membranous tissue and the frictional force between the second supporting member and the membranous tissue results mainly from the difference in thickness between the first supporting member and the second supporting member. Thus, it was possible to transfer the membranous tissue without damage to it. Incidentally, it was more difficult to adhere the transferring tool closely to the sharply bent surface of the artificial organ on account of the thick second supporting member.

Example 3

Experiment with Films of Dissimilar Materials, in which the Position for Transfer is a Non-Pulsating Bovine Heart

Example 3-1

The first supporting member: 25-μm thick film of polyurethane

The second supporting member: 68-μm thick film of polyethylene

Membranous tissue: sheet-shaped cell culture prepared from human myoblasts

Position for transfer: bovine heart (not pulsating)

Method: A transferring tool was prepared and composed of the first supporting member and the second supporting member, with the membranous tissue (kept wet with water) held between them. Transfer was accomplished by the method shown in FIGS. 2A to 2C.

Result: In the step shown in FIG. 2B, it was possible to remove the second supporting member alone while keeping the membranous tissue stationary. Thus, it was possible to transfer the membranous tissue without damage to the membranous tissue. The transferring tool easily deformed to closely adhere to the surface of the bovine heart which had been extracted, even though the surface was sharply bent.

Example 4

Experiment with Films of Dissimilar Materials, in which the Position for Transfer is a Pulsating Pig Heart

Example 4-1

The first supporting member: 10-μm thick film of polyurethane

The second supporting member: 30-μm thick film of polyethylene

Membranous tissue: sheet-shaped cell culture prepared from mouse fibroblasts (NIH3T3 cells)

Position for transfer: pig heart (pulsating)

Method: A transferring tool was prepared and composed of the first supporting member and the second supporting member, with the membranous tissue (kept wet with water) held between them. Transfer was accomplished by the method shown in FIGS. 2A to 2C.

Result: In the step shown in FIG. 2B, it was possible to remove the second supporting member alone while keeping the membranous tissue stationary. Thus, it was possible to transfer the membranous tissue without damage to the membranous tissue.

Example 4-2

The first supporting member: 10-μm thick film of polyurethane

The second supporting member: 68-μm thick film of polyethylene

Membranous tissue: sheet-shaped cell culture prepared from mouse fibroblasts (NIH3T3 cells)

Position for transfer: pig heart (pulsating)

Method and result: Same as those of Example 4-1.

Example 4-3

The first supporting member: 25-μm thick film of polyurethane

The second supporting member: 68-μm thick film of polyethylene

Membranous tissue: sheet-shaped cell culture prepared from mouse fibroblasts (NIH3T3 cells)

Position for transfer: pig heart (pulsating)

Method and result: Same as those of Example 4-1. The first supporting member was rapidly removed after the second supporting had been removed. In this way, it was possible to protect the sheet-shaped cell culture (which was prepared from mouse fibroblasts) from damage by pulsation.

Example 4-4

The first supporting member: 25-μm thick film of polyurethane

The second supporting member: 68-μm thick film of polyethylene

Membranous tissue: sheet-shaped cell culture prepared from pig myoblasts

Position for transfer: pig heart (pulsating)

Method and result: Same as those of Example 4-1

Example 4-5

The first supporting member: 25-μm thick film of polyurethane

The second supporting member: 68-μm thick film of polyethylene

Membranous tissue: sheet-shaped cell culture prepared from human myoblasts

Position for transfer: pig heart (pulsating)

Method and result: Same as those of Example 4-1

Table 1 below shows the handleability and adhesion to curved surfaces of the transferring tools in Examples 4-1 to 4-5. The larger the number of + signs, the better the handleability and adhesion to curved surfaces, while the lesser the number of + signs, the lower the handleability and adhesion to curved surfaces. The supporting members have good handleability, which means that handling of the membranous tissue by the supporting members is good. For example, the membranous tissue can be easily carried and transferred to the position for transfer, and the supporting members can be removed easily from the transferred membranous tissue. Good adhesion to curved surfaces means that the supporting members easily conform to an irregular surface and to movement of an object targeted for transfer.

TABLE 1

| Example | 4-1 | 4-2 | 4-3 | 4-4 | 4-5 |
|---|---|---|---|---|---|
| Handleability | ++ | ++ | +++ | +++ | +++ |
| Adhesion to curved surface | +++ | ++ | ++ | ++ | ++ |

The Second Embodiment

Figure 4:
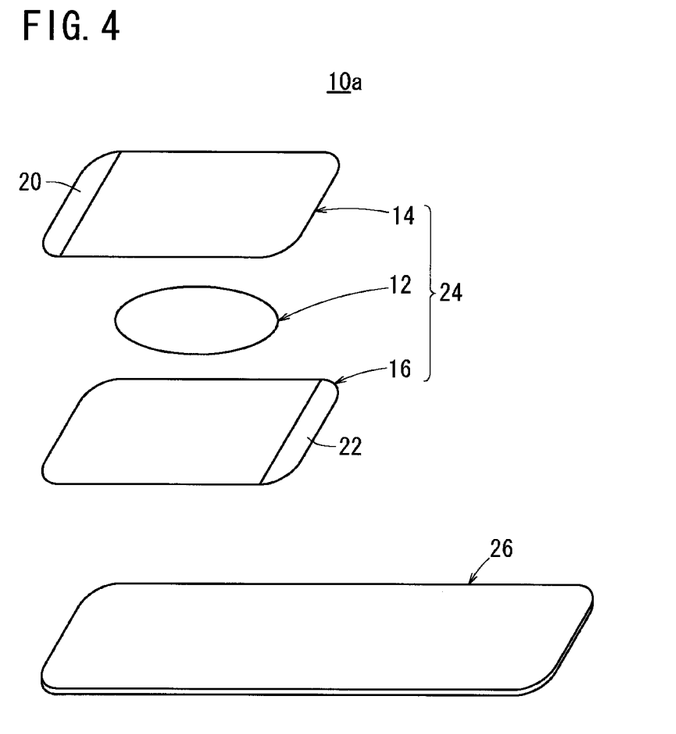
FIG. 4 is an exploded perspective view showing an example of a tool for transferring a membranous tissue according to a second embodiment of the presently disclosed subject matter.

FIG. 4 is an exploded perspective view showing a tool 10a for transferring a membranous tissue according to a second embodiment of the presently disclosed subject matter. (This tool will be simply referred to as the transferring tool 10a hereinafter.) The transferring tool 10a according to the second embodiment has those elements which function as well or in the same way as those elements of the transferring tool 10 according to the first embodiment. Such elements are indicated by identical reference numbers without repeated explanation.

The transferring tool 10a according to the second embodiment differs from the transferring tool 10 according to the first embodiment in that the former additionally has a third supporting member 26. In other words, the transferring tool 10a includes a holding unit 24 (which includes the first supporting member 14 and the second supporting member 16, with the membranous tissue 12 held between them) and a third supporting member 26 on which the holding unit 24 is placed.

The third supporting member 26 is larger than the first and second supporting members 14 and 16. This structure provides a part that permits one to grasp only the third supporting member 26 on which the holding unit 24 is not placed while the holding unit 24 is placed on the other part of the third supporting member 26. To be more specific, the third supporting member 26 can be an approximately rectangular sheet which is longer than the first and second supporting members 14 and 16, so that one end thereof can be grasped when the holding unit 24 is placed on that part thereof which is close to the other end thereof. Incidentally, the third supporting member 26 may take on shapes other than a rectangle, such as circle, ellipse, square, non-symmetrical shapes, and other shapes depending on particular application.

The third supporting member 26 may be formed from at least one material (possibly selected from those materials exemplified for the first and second supporting members 14 and 16) and metal. The material can be formed to be stiff enough to greatly resist bending when the third supporting member 26 is grasped by its one end, with the holding unit 24 placed on that part of the third supporting member 26 which is close to the other end thereof. For this reason, the third supporting member 26 can be thicker than the first and second supporting members 14 and 16, say, 100 μm to 2000 μm, and possibly 200 μm to 1000 μm.

Figure 5A:
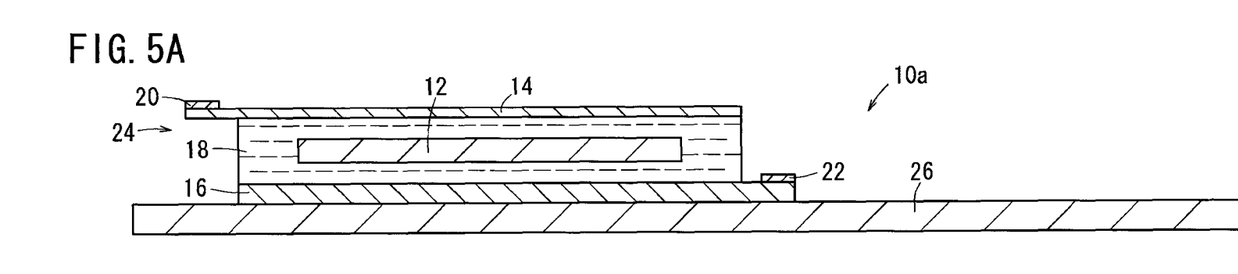
FIG. 5A is a diagram illustrating an example of a first process in an exemplary procedure for transferring a membranous tissue to a desired position for transfer by using the tool for transferring a membranous tissue as shown in FIG. 4.

The transferring tool 10a constructed as mentioned above can used in the following way to transfer the membranous tissue 12 to the position for transfer. The transferring tool 10a is composed of the first supporting member 14, the membranous tissue 12, the second supporting member 16, and the third supporting member 26, which are sequentially arranged downward, as shown in FIG. 5A. Firstly, the transferring tool 10a is transported to the position for transfer S. Here, the holding unit 24 can be transported simply and stably because, during transportation, the holding unit 24 is placed on the third supporting member 26 which is relatively stiff.

Figure 5B:
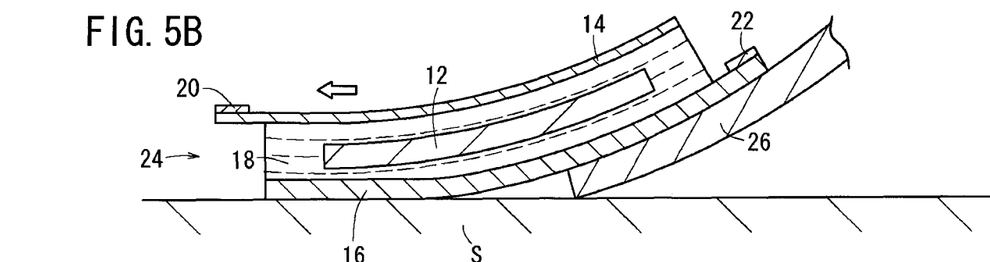
FIG. 5B is a diagram illustrating an example of a second process in the procedure.
Figure 5C:
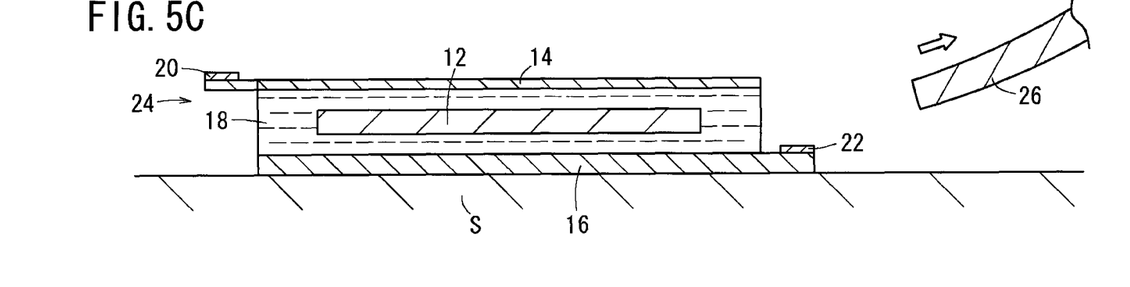
FIG. 5C is a diagram illustrating an example of a third process in the procedure.

Next, as shown in FIG. 5B, the holding unit 24 is slid relative to the third supporting member 26, with the fore-end of the third supporting member 26 kept in contact with the position for transfer S. By sliding the holding unit 24, the holding unit 24 is placed on the position for transfer S, as shown in FIG. 5C. After the holding unit 24 has been placed on the position for transfer S, the third supporting member 26 is removed.

Incidentally, that side of the third supporting member 26 on which the holding unit 24 is placed and/or the lower side of the second supporting member 16 can have surface treatment to impart an hydrophilic nature or to reduce frictional force. With the surface treatment, the frictional force at the contact surfaces between the second supporting member 16 and the third supporting member 26 can be reduced, and the third supporting member 26 can slide easily and smoothly relative to the second supporting member 16.

After the third supporting member 26 has been removed, the second supporting member 16 can be removed from between the membranous tissue 12 and the position for transfer S, in the same way as shown in FIG. 2B. Finally, the first supporting member 14 can be removed from the top of the membranous tissue 12 in the same way as shown in FIG. 2C or FIG. 2D. In this way, the transfer of the membranous tissue 12 to the position for transfer S is completed. As explained above, the transferring tool 10a according to this embodiment also permits the transfer of the membranous tissue 12 to the position for transfer S in an easy and secure way without damage to the membranous tissue 12.

The second embodiment mentioned above has constituents common to those in the first embodiment, and they produce the same action and effect as in the first embodiment, as a matter of course.

The second embodiment is demonstrated by Example 5 mentioned below.

Example 5

Experiment with Films of Dissimilar Materials, in which the Position for Transfer is a Curved Surface Example 5-1

The first supporting member: 25-μm thick film of polyurethane

The second supporting member: 68-μm thick film of polyethylene

The third supporting member: 195-µm thick film of polypropylene

Membranous tissue: sheet-shaped cell culture prepared from human myoblasts

Position for transfer: artificial heart (clay wrapped in food-wrapping film), having a curved surface.

Method: A transferring tool was prepared and composed of the first supporting member and the second supporting member, with the membranous tissue (kept wet with water) held between them, and with the third supporting member on which the foregoing assembly is placed. Transfer was accomplished by the method shown in FIGS. 5A and 5B and FIGS. 2A to 2C.

Result: The third supporting member, which is relatively stiff compared to the first and/or second supporting member(s), facilitated the transfer of the films (holding the membranous tissue between them) to the position for transfer. The sliding of the third supporting member relative to the first supporting member, the membranous tissue, and the second supporting member (as shown in FIG. 5B) did not move the membranous tissue, which remained on the first supporting member. Likewise, the sliding of the second supporting member relative to the first supporting member and the membranous tissue (as shown in FIG. 2B) did not move the membranous tissue, which remained on the first supporting member. The first supporting member was finally peeled off from the membranous tissue while the membranous tissue remained on the position for transfer.

Other Embodiments

According to the first and second embodiments mentioned above, the first supporting member 14 is thinner than the second supporting member 16, so that the frictional force P1 between the first supporting member 14 and the membranous tissue 12 is greater than the frictional force P2 between the second supporting member 16 and the membranous tissue 12. The difference in frictional force may be created by other mechanisms which resort to difference in bulk modulus or difference in water absorptivity.

With regard to difference in bulk modulus, according to the formula (3) above, there is a fact that the greater the bulk modulus, the greater the cohesive force. The fact suggests that, proper materials would be selected such that the first supporting member 14 has a larger bulk modulus than the second supporting member 16, whereby the frictional force P1 between the first supporting member 14 and the membranous tissue 12 would be larger than the frictional force P2 between the second supporting member 16 and the membranous tissue 12.

Figure 6A:
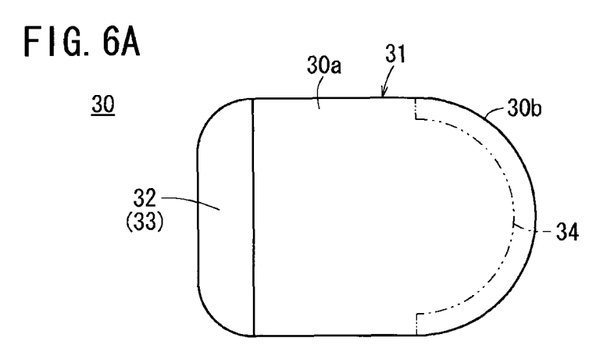
FIG. 6A is a plan view showing an example of a supporting member pertaining to the first example of structure.
Figure 6B:
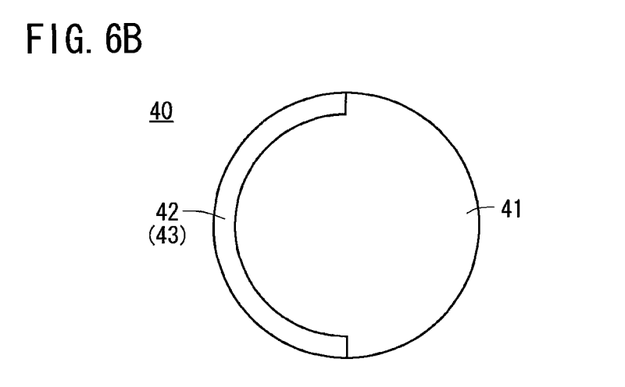
FIG. 6B is a plan view showing an example of a supporting member pertaining to the second example of structure.
Figure 6C:
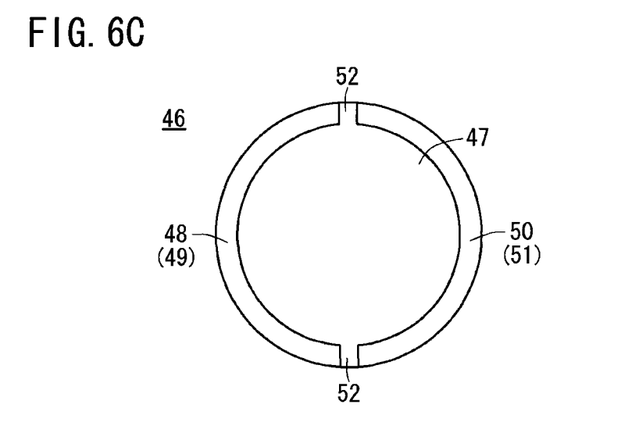
FIG. 6C is a plan view showing an example of a supporting member pertaining to the third example of structure.

In addition, the first and second supporting members 14 and 16 mentioned above may be replaced by the supporting members 30, 40, and 46 as shown in FIGS. 6A to 6C.

The supporting member 30 shown in FIG. 6A is composed of the sheet body 31 (as the main body) and the grip 32 attached to one end thereof. The sheet body 31 is composed of a square part 30a at one end and a half-rounded part 30b at the other end. The grip 32 is stiffer than the sheet body 31. In the illustrated example, the grip 32 is a liner form formed by attaching a straight reinforcing sheet 33 to the edge of the square part 30a. In addition to or in place of the grip 32, the crescent-shaped grip 34 may be attached to the edge of the half-rounded part 30b.

The supporting member 40 shown in FIG. 6B is composed of the circular sheet body 41 (as the main body) and the crescent-shaped grip 42 which is attached to a portion of the edge of the sheet body 41. (This portion covers about 180 degrees along the circumference in FIG. 6B.) The grip 42 is stiffer than the sheet body 41. In the illustrated example, the grip 42 is formed by attaching a crescent-shaped reinforcing sheet 43 to the edge of the sheet body 41. The supporting member 40 may be elliptic rather than circular. In addition, the crescent-shaped grip 42 may be divided into two or more sections along the circumference.

The supporting member 46 shown in FIG. 6C is composed of the sheet body 47 (as the main body) and the crescent-shaped grips 48 and 50 which respectively cover the two halves of the circumference of the sheet body 47. The grips 48 and 50 are stiffer than the sheet body 47. In the illustrated example, they are formed by attaching reinforcing sheets 49 and 51 to the edge of the sheet body 47. The grips 48 and 50 are separated from each other by narrow non-reinforcing parts 52. The grips 48 and 50 can extend over a broad range to permit the supporting member 46 to be gripped in any direction for smooth movement. In addition, in the case where the supporting member 46 is used as the first supporting member 14 and the first supporting member 14 is folded back to peel off, for example, the non-reinforcing parts 52 permits the first supporting member 14 to be bent sharply (as shown in FIG. 2C) when the first supporting member 14 is folded in half. Such sharp bending reduces the surface tension. Therefore, the supporting member 46 having the grips 48 and 50, which are separated from each other by the non-reinforcing parts 52, permits the membranous tissue 12 to be peeled off more easily from the supporting member 14 than an other supporting member (not shown) having the grips formed over the entire circumference. Moreover, the supporting member 46 may be elliptic rather than circular.

In the case illustrated in FIGS. 6A to 6C, the reinforcing sheets 33, 43, and 49 may be peeled off from the sheet bodies 31, 41, and 47 during use according to need.

Certain exemplary embodiments of the presently disclosed subject matter have been described above; they are not intended to restrict the scope of the presently disclosed subject matter. The presently disclosed subject matter may be variously changed and modified within the scope thereof, as a matter of course.

What is claimed is:

1. A tool for transferring a membranous tissue composed of cells, the tool comprising:
    a first sheet-shaped supporting member disposed on one side of the membranous tissue in a wet state; and
    a second sheet-shaped supporting member disposed on an other side of the membranous tissue in a wet state, wherein
    the first supporting member and the second supporting member are configured to entirely hold the membranous tissue, and
    the first supporting member and the second supporting member are configured such that a frictional force between the first supporting member and the membranous tissue is larger than a frictional force between the second supporting member and the membranous tissue,
    wherein at least one of the first supporting member and the second supporting member has a grip formed as a sheet of material bonded to a peripheral edge of at least one of the first supporting member and the second supporting member.

2. The tool for transferring the membranous tissue as defined in claim 1, wherein the first supporting member is thinner than the second supporting member.

3. The tool for transferring the membranous tissue as defined in claim 1, wherein the first supporting member is more flexible than the second supporting member.

4. The tool for transferring the membranous tissue as defined in claim 1, further comprising:
a third supporting member which is stiffer than the second supporting member, the third supporting member configured to support thereon a holding unit which is composed of the first supporting member and the second supporting member and the membranous tissue held between them.

5. The tool for transferring the membranous tissue as defined in claim 1, further comprising:
a preserving liquid located between the first supporting member and second supporting member.

6. The tool for transferring the membranous tissue as defined in claim 1, wherein the first supporting member is comprised from a material different from a material that comprises the second supporting member.

7. The tool for transferring the membranous tissue as defined in claim 6, wherein the first supporting member is a polyurethane sheet, and the second supporting member is a polyethylene sheet.

8. A method for transferring a membranous tissue composed of cells using the tool of claim 1, the method comprising:
providing the tool for transferring the membranous tissue, the tool having the first sheet-shaped supporting member disposed on the one side of the membranous tissue in the wet state and the second sheet-shaped supporting member disposed on the other side of the membranous tissue in the wet state, wherein the first supporting member and the second supporting member entirely hold the membranous tissue, and are configured such that the frictional force between the first supporting member and the membranous tissue is larger than the frictional force between the second supporting member and the membranous tissue;
arranging the tool for transferring the membranous tissue on a position to which the membranous tissue is to be transferred;
sliding the second supporting member relative to the membranous tissue, thereby removing the second supporting member from between the membranous tissue and the position to which the membranous tissue is to be transferred; and
removing the first supporting member from the membranous tissue while leaving the membranous tissue on the position to which the membranous tissue is to be transferred.

9. The method for transferring a membranous tissue as defined in claim 8, wherein removing the first supporting member includes peeling the first supporting member back over itself.

10. The method for transferring a membranous tissue as defined in claim 8, further comprising:
providing a preserving liquid between the first supporting member and second supporting member.

11. The method for transferring a membranous tissue as defined in claim 8, further comprising:
providing a third sheet-shaped supporting member; and removing the first supporting member and second supporting member from the third supporting member prior to sliding the second supporting member relative to the membranous tissue.

12. The method for transferring a membranous tissue as defined in claim 8, wherein providing the tool for transferring the membranous tissue includes providing at least one of the following:
the first supporting member comprised of a material different from a material of the second supporting member;
the first supporting member thinner than the second supporting member; and
the first supporting member more flexible than the second supporting member.

13. A method for transferring a membranous tissue composed of cells using the tool of claim 1, the method comprising:
providing the tool for transferring the membranous tissue, the tool having the first sheet-shaped supporting member disposed on the one side of the membranous tissue in the wet state and the second sheet-shaped supporting member disposed on the other side of the membranous tissue in the wet state, wherein the first supporting member and the second supporting member entirely hold the membranous tissue, and are configured such that the frictional force between the first supporting member and the membranous tissue is larger than the frictional force between the second supporting member and the membranous tissue;
arranging the tool for transferring the membranous tissue substantially at a position to which the membranous tissue is to be transferred;
sliding the first supporting member and membranous tissue relative to the second supporting member, thereby placing the first supporting member and membranous tissue on the position to which the membranous tissue is to be transferred; and
removing the first supporting member from the membranous tissue while leaving the membranous tissue on the position to which the membranous tissue is to be transferred.

14. The method for transferring a membranous tissue as defined in claim 13, wherein removing the first supporting member includes peeling the first supporting member back over itself.

15. The method for transferring a membranous tissue as defined in claim 13, further comprising:
providing a preserving liquid between the first supporting member and second supporting member.

16. The method for transferring a membranous tissue as defined in claim 13, wherein the position to which the membranous tissue is to be transferred is located on a target tissue, and wherein sliding the first supporting member and membranous tissue relative to the second supporting member includes,
keeping a majority of a surface of the second supporting member which faces the position to which the membranous tissue is to be transferred spaced from the target body.

17. The method for transferring a membranous tissue as defined in claim 13, wherein providing the tool for transferring the membranous tissue includes providing at least one of the following:
the first supporting member comprised of a material different from a material of the second supporting member;
the first supporting member thinner than the second supporting member; and
the first supporting member more flexible than the second supporting member.

18. A tool for transferring a membranous tissue composed of cells, the tool comprising:
a first sheet-shaped supporting member disposed on one side of the membranous tissue in a wet state; and a second sheet-shaped supporting member disposed on an other side of the membranous tissue in a wet state, wherein the first supporting member and the second supporting member are configured to entirely hold the membranous tissue, and the first supporting member and the second supporting member are configured such that a frictional force between the first supporting member and the membranous tissue is larger than a frictional force between the second supporting member and the membranous tissue, wherein at least one of the first supporting member and the second supporting member has a grip, which is stiffer than other parts, on at least a portion of an edge of a respective one of the first supporting member and the second supporting member.

19. A kit for transferring a membranous tissue composed of cells, comprising:

a membranous tissue;

a preserving liquid; and a first sheet-shaped supporting member disposed on one side of the membranous tissue in a wet state, and a second sheet-shaped supporting member disposed on an other side of the membranous tissue in a wet state, wherein the first supporting member and the second supporting member are configured to entirely hold the membranous tissue, and the first supporting member and the second supporting member are configured such that a frictional force between the first supporting member and the membranous tissue is larger than a frictional force between the second supporting member and the membranous tissue, wherein at least one of the first supporting member and the second supporting member has a grip, and the grip is at least one of:

formed as a sheet of material bonded to a peripheral edge of at least one of the first supporting member and the second supporting member; and stiffer than other parts, on at least a portion of an edge of a respective one of the first supporting member and the second supporting member.

* * * * *